US00PP29916P2

(12) United States Plant Patent
O'Connell

(10) Patent No.: US PP29,916 P2
(45) Date of Patent: Nov. 27, 2018

(54) ***GRAPTOVERIA* PLANT NAMED 'PETRA'S BEAUTY'**

(50) Latin Name: ***Graptoveria* hybrid**
Varietal Denomination: PETRA'S BEAUTY

(71) Applicant: Altman Specialty Plants, Inc., Vista, CA (US)

(72) Inventor: Renee O'Connell, Escondido, CA (US)

(73) Assignee: Altman Specialty Plants, Inc., Vista, CA (US)

( * ) Notice: Subject to any disclaimer, the term of this patent is extended or adjusted under 35 U.S.C. 154(b) by 0 days.

(21) Appl. No.: 15/732,297

(22) Filed: Oct. 19, 2017

(51) Int. Cl.
*A01H 5/12* (2018.01)

(52) U.S. Cl.
USPC ..... Plt./373

(58) Field of Classification Search
USPC ..... Plt./373
See application file for complete search history.

*Primary Examiner* — Annette H Para
(74) *Attorney, Agent, or Firm* — Cassandra Bright

(57) ABSTRACT

A new and distinct *Echeveria* cultivar named 'Petra's Beauty' is disclosed, characterized by thickened, silvered dark purple-green leaves with the apices blushed with a color that is similar in appearance to a metallic rose. The new cultivar can be grown in a variety of pot sizes, from 2.5 inch through 2 gallon, due to free offsetting in combination with a compact plant morphology. The new cultivar 'Petra's Beauty' can be propagated by leaf cuttings. The new variety is a *Graptoveria, cheveria*, part of the Crassulaceae complex that includes *Aeonium, Crassula, Graptopetalum, Pachyphytum, Sedum* and others. The new variety would typically be produced as a container plant for the patio or as landscape plants, as well as a variety of ornamental purposes.

1 Drawing Sheet

Latin name of the genus and species: *Graptoveria* hybrid.
Variety denomination: 'PETRA'S BEAUTY'.

BACKGROUND OF THE INVENTION

The new cultivar, *Graptoveria* 'PETRA'S BEAUTY', is the product of a planned breeding program. The new variety originated as a naturally occurring whole plant mutation of the proprietary, unpatented, seed parent, *Graptoveria* 'Royal Flush'. The new cultivar 'PETRA'S BEAUTY' was discovered by the inventor, Renee O'Connell, in January 2015, in Vista, Calif. at a commercial greenhouse.

Asexual reproduction of the new cultivar 'PETRA'S BEAUTY' was first performed January, 2015 in Vista, Calif., at a commercial greenhouse, by terminal vegetative cuttings. *Graptoveria* 'PETRA'S BEAUTY' has since produced multiple generations and has shown that the unique features of this cultivar are stable and reproduced true to type.

SUMMARY OF THE INVENTION

The cultivar 'PETRA'S BEAUTY' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'PETRA'S BEAUTY'. These characteristics in combination distinguish 'PETRA'S BEAUTY' as a new and distinct *Graptoveria* cultivar:

1 Thickened, silvered dark purple-green leaves with the apices blushed with a color that is similar in appearance to a metallic rose.

2. Adapability to multiple pot sizes; as small as 2.5", but it will fill a 2 gallon pot as it offsets to form larger clusters.
3. *Graptoveria* 'Petra's Beauty' can be propagated by leaf cuttings, enhancing propagation in a commercial nursery.
4. *Graptoveria* 'Petra's Beauty', due to the unusual nearly metallic rose highlight of the leaves, can be readily utilized for decorative projects such as bridal bouquets, dish gardens, holiday centerpieces and others.

PARENTAL COMPARISON

Plants of the new cultivar are similar to plants of the parent, in most horticultural characteristics, however, plants of the new cultivar differ in the following;

1. *Graptoveria* 'Petra's Beauty' displays silvered dark purple-green leaves blushed with a near metallic rose, whereas *Graptoveria* 'Royal Flush' produces leaves that are a dull purple green with a glaucous overlay
2. *Graptoveria* 'Petra's Beauty' forms rosettes of a wider, more flattened morphology, whereas *Graptoveria* 'Royal Flush' produces rosettes that are not as wide, and with the leaves upswept towards the center.
3. *Graptoveria* 'Petra's Beauty' displays leaves that are more flattened, whereas the leaves of *Graptoveria* 'Royal Flush' are much more chunky and rounded.
4. The inflorescence of *Graptoveria* 'Petra's Beauty' is more upright than the inflorescence of *Graptoveria* 'Royal Flush'.
5. The inflorescence of *Graptoveria* 'Petra's Beauty' exhibits conspicuous bracts, blushed ruby pink in bright light, whereas the bracts of *Graptoveria* 'Royal Flush' are not nearly so conspicuous, and do not display the ruby pink blushing in bright light.

COMMERCIAL COMPARISON

The new cultivar 'Petra's Beauty' can be compared to the unpatented commercial variety *Graptoveria* 'Debbie'. Plants of the *Graptoveria* 'Debbie' are similar to plants of the new cultivar 'Petra's Beauty' in most horticultural characteristics. However, the new cultivar 'Petra's Beauty' differs in the following:

1. *Graptoveria* 'Petra's Beauty' displays rosettes of silvered violet green leaves, blushed with a near metallic rose, whereas the rosette of *Graptoveria* 'Debbie' is a pruinose violet, with no near metallic rose blush.
2. *Graptoveria* 'Petra's Beauty' produces upright, complex inflorescences of with conspicuous bracts, whereas *Graptoveria* 'Debbie' produces lax inflorescences without conspicuous bracts.
3. *Graptoveria* 'Petra's Beauty' produces fleshy, glabrous leaves, whereas *Graptoveria* 'Debbie' produces longer, less fleshy leaves with pruinose epidermis.
4. *Graptoveria* 'Petra's Beauty' branches to form an upward growing plant that can fill a 8" or 2 gallon pot, whereas *Graptoveria* 'Debbie' produces a rosette of low morphology, therefore is not a candidate for an 8" or 2 gallon pot.

The new cultivar 'Petra's Beauty' can be compared to the unpatented commercial variety *Graptoveria* 'Opalina'. Plants of *Graptoveria* 'Opalina' are similar to plants of the new cultivar 'Petra's Beauty' in most horticultural characteristics. However, plants of the new cultivar 'Petra's Beauty' differ in the following:

1. *Graptoveria* 'Petra's Beauty' produces fleshy, glabrous leaves, whereas *Graptoveria* 'Opalina' produces leaves that are more rounded, with pruinose epidermis.
2. *Graptoveria* 'Opalina' displays rosettes of whitish aqua leaves, whereas *Graptoveria* 'Petra's Beauty' exhibits rosettes of silvered violet green leaves.
3. *Graptoveria* 'Petra's Beauty' displays a near metallic rose blushing of the leaves, whereas *Graptoveria* 'Opalina' produces pruinose aqua leaves, devoid of any metallic blushing of the leaves.
4. *Graptoveria* 'Petra's Beauty' grows faster than *Graptoveria* 'Opalina'.

BRIEF DESCRIPTION OF THE PHOTOGRAPH

The accompanying photograph illustrates in full color a typical plant of 'PETRA'S BEAUTY' grown in a greenhouse in Vista, Calif. The photograph was taken using conventional techniques and equipment. While the colors in this photograph may display variances of color as compared to the living cultivar, due to LRV (light reflectance value), they are as accurate as possible using conventional photographic techniques. Colors in the photograph may appear to differ slightly from the color values cited in the botanical description, which accurately describe the colors of the new *Echeveria* plant. The included photograph depicts plants grown under natural light conditions of 2500-4000 footcandles. Temperatures ranged from −1° C. to 29° C. night and day. No artificial light, photoperiodic treatments or chemical treatments were given to the plants.

DETAILED BOTANICAL DESCRIPTION

In the following description, color references are made to The Royal Horticultural Society Colour Chart, except where general terms of ordinary dictionary significance are used. The following observations and measurements describe 'Petra's Beauty' plants in a commercial greenhouse in Vista, Calif. Temperatures ranged from −1° C. to 29° C. night and day. No artificial light, photoperiodic treatments or chemical treatments were given to the plants. Natural light conditions were approximately 2500 to 4000 fc of light. Measurements and numerical values represent averages of typical plant types.

Botanical classification: *Echeveria* hybrid 'PETRA'S BEAUTY'.

PROPAGATION

Type of propagation typically used: Terminal vegetative cuttings.

Time to initiate roots: About 11 days at approximately 24° C.

Root description: Fibrous.

PLANT

Age of plant described: Approximately 6 months from a cutting.

Container size of the plant described: 1 gallon.

Growth habit: Upright rosulate plant.

Height: Approximately 10 cm to top of foliage, approximately 35 cm to top of flowering plane.

Plant spread: Approximately 15 to 18 cm.

Growth rate: Moderate to rapid.

Branching characteristics: Not typically observed.

Foliage:

*Arrangement.*—Rosulate.

*Average length.*—8 cm.

*Average width.*—2.8 cm.

*Width at base.*—Average 1.2 cm.

*Aspect of leaf.*—Leaf slightly cupped upward.

*Leaf thickness.*—About 1.2 cm at thickest point at center of leaf.

*Shape of blade.*—Spatulate.

*Apex.*—Broad mucronate. Mucronate tip 2 to 3 mm long, not sharp.

*Base.*—Attenuate.

*Margin.*—Entire.

*Texture of top surface.*—Glabrous. Slightly metallic glaucous.

*Texture of bottom surface.*—Glabrous. Slightly metallic glaucous.

*Appearance of top surface.*—Matte and metallic.

*Appearance of bottom surface.*—Matte and metallic.

*Quantity of leaves per plant.*—Average range 40 to 55.

*Color.*—Young foliage upper side: Near RHS Green 138B. Apical margin coloration near Red 51A. Base Yellow-Green 145D. Young foliage under side: Near RHS Green 138B. Apical margin near Red 51A. Upper section flushed Red 51A. Base Yellow-Green 145D. Mature foliage upper side: Near RHS Green N138D. Apical margin coloration near Red 51B. Upper section lightly flushed Greyed-Purple N187C, creating a metallic appearance. Base Yellow-Green 145D. Mature foliage, under side: Near RHS Green N138D. Apical margin coloration near Red 51B. Upper section flushed Red 51C. Base Yellow-Green 145D.

FLOWER

Natural flowering season: Summer though Fall.
Inflorescence type: Raceme.
Rate of flower opening: About 2 weeks to a fully open flower.
Flower longevity on plant: About 14 to 24 days, depending upon ambient temperatures.
Quantity of flowers: About 3 to 5 individual flowers and 5 to 7 buds.
*Total Inflorescence size*.—Height: Approximately 10 to 15 cm. Width: Approximately 6 to 7 cm.
*Corolla*.—Arrangement: Pentagonal, tightly held, fused at base. Size: Length: Approximately 1.5 cm. Width: Approximately 1.0 cm at widest point.
Petals:
*Quantity*.—5.
*Length*.—Approximately 1.4 cm.
*Width*.—Approximately 0.35 cm.
*Margin*.—Entire.
*Shape*.—Narrow elliptic.
*Apex*.—Acute.
*Base*.—Fused at bottom 10% of length.
*Texture*.—Glabrous, all surfaces.
Color:
*When opening*.—Outer surface: Near RHS Orange-Red 35A. Inner surface: Near RHS Red 53D.
*Fully opened*.—Outer surface: Near RHS Red 43A, base 43D. Inner surface: Near RHS Red 55A streaked 56D.
*Color changes when aging*.—Outer surface: Near RHS Red 42B. Inner surface: Near RHS Red 39A.
Bud: (near opening):
*Shape*.—Wide conical.
*Length*.—Approximately 1.0 cm.
*Diameter*.—Approximately 1.0 cm.
*Color*.—Near Red 43C, lightly flushed Greyed-Purple N187C.
Sepals:
*Length*.—1.0 to 1.5 cm.
*Width*.—3 to 5 mm.
*Margin*.—Entire.
*Shape*.—Narrow deltate.
*Apex*.—Acute.
*Base*.—Truncate.
*Texture*.—Glabrous, upper and lower surfaces.
*Appearance*.—Very slightly shiny, upper and lower surfaces.
*Color*.—Outer: Near Green 137D, apex near Greyed-Purple 187B. Inner: Near Green 137C, apex near Greyed-Purple 187B.
Peduncle:
*Length*.—Average range 10 to 15 cm.
*Width*.—Approximately 8 mm.
*Strength*.—Strong.
*Texture*.—Glabrous.
*Color*.—Lower section near RHS Red 39D flushed 39A, upper section near Yellow-Green 145C.
Pedicels:
*Length*.—Average range 2.5 to 3.0 cm.
*Width*.—Approximately 3 mm.
*Strength*.—Moderately strong.
*Texture*.—Glabrous.
*Color*.—Near RHS Orange-White 159A.
Bracts:
*Length*.—1 to 2 cm.
*Width*.—6 to 9 mm.
*Margin*.—Entire.
*Shape*.—Ovate.
*Apex*.—Acute.
*Base*.—Truncate.
*Texture*.—Glabrous, upper and lower surfaces.
*Appearance*.—Very slightly shiny, upper and lower surfaces.
*Color*.—Upper: Near Greyed-Orange 166B, base near Green 138B. Lower: Near RHS Green 138A apex near Greyed-Red 178A.
*Fragrance*.—None detected.

REPRODUCTIVE ORGANS

Stamens: (Androecium).
*Number*.—Most commonly 10.
*Filament length*.—Approximately 0.5 cm.
*Filament color*.—Near RHS Greyed-Purple 183D.
*Anther length*.—0.1 cm.
*Anther color*.—Near RHS Greyed-Purple 183A.
*Anther shape*.—Linear.
*Pollen*.—Not observed.
Pistil: (Gynoecium).
*Number*.—Average 5.
*Length*.—Approximately 9 mm.
*Style color*.—Near White N155C, lightly flushed Red 52B.
*Stigma*.—Shape: Linear. Color: Near RHS Red 53A. Ovary Color: Near RHS White N155B.

OTHER CHARACTERISTICS

Fruits and seeds: Typical to Genus. Minute, less than 1 mm dry seeds. Colored between black and brown, too small to accurately measure with color chart.
Temperature tolerance: Tolerates temperatures from approximately −2° C. to at least 35° C.
Disease/pest resistance: Neither resistance or susceptibility to other normal diseases and pests of *Graptoveria* has been observed.
Drought tolerance: Tolerates at least 3 weeks of high temperatures without supplemental water, showing no serious damage to plant.

What is claimed is:

1. A new and distinct cultivar of *Echeveria* plant named 'PETRA'S BEAUTY' as herein illustrated and described.

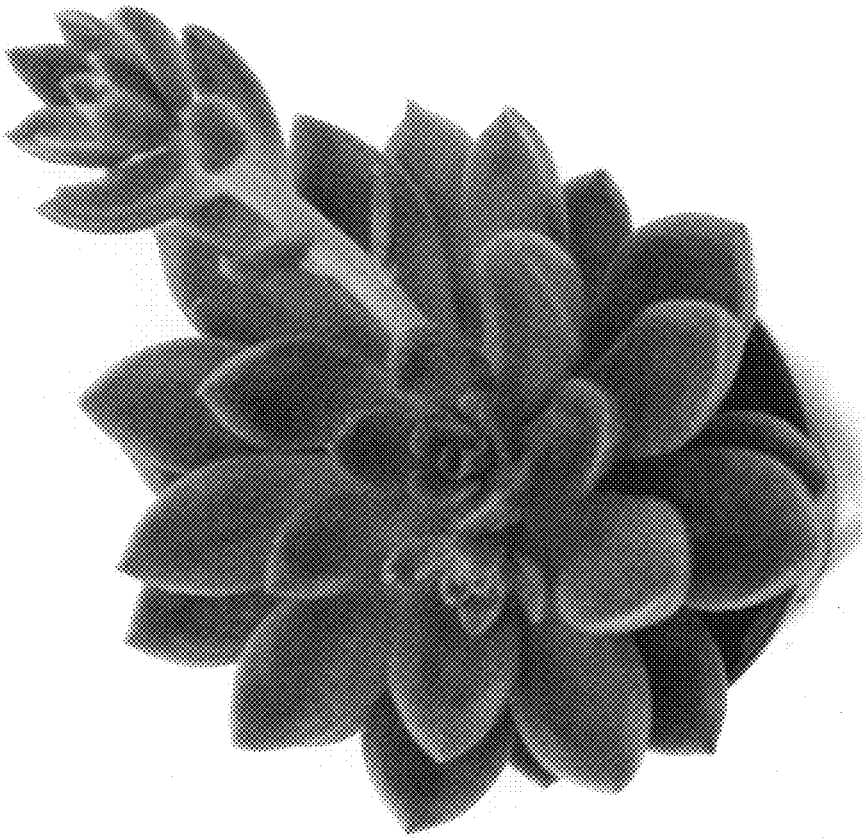

* * * * *